United States Patent
Defrance et al.

(10) Patent No.: US 10,421,717 B2
(45) Date of Patent: Sep. 24, 2019

(54) PROCESS FOR PREPARING BRIVARACETAM

(71) Applicant: UCB Biopharma SPRL, Brussels (BE)

(72) Inventors: Thierry Defrance, Brussels (BE); Jean Septavaux, Marseilles (FR); Didier Nuel, Marseilles (FR)

(73) Assignee: UCB Biopharma SPRL, Brussels (BE)

( * ) Notice: Subject to any disclaimer, the term of this patent is extended or adjusted under 35 U.S.C. 154(b) by 0 days.

(21) Appl. No.: 15/772,607

(22) PCT Filed: Oct. 27, 2016

(86) PCT No.: PCT/EP2016/075935
§ 371 (c)(1),
(2) Date: May 1, 2018

(87) PCT Pub. No.: WO2017/076738
PCT Pub. Date: May 11, 2017

(65) Prior Publication Data
US 2019/0119206 A1    Apr. 25, 2019

(30) Foreign Application Priority Data
Nov. 3, 2015 (EP) ..................... 15192760

(51) Int. Cl.
*C07D 207/27* (2006.01)
*C07D 207/26* (2006.01)

(52) U.S. Cl.
CPC ......... *C07D 207/27* (2013.01); *C07D 207/26* (2013.01)

(58) Field of Classification Search
None
See application file for complete search history.

(56) References Cited

FOREIGN PATENT DOCUMENTS

| WO | WO-2001/062726 A2 | 8/2001 |
| WO | WO-2005/028435 | 3/2005 |
| WO | WO-2009/053446 | 4/2009 |

OTHER PUBLICATIONS

International Search Report dated Jan. 24, 2017 issued in PCT/EP2016/075935.
Written Opinion dated Jan. 24, 2017 issued in PCT/EP2016/075935.

*Primary Examiner* — Kamal A Saeed
(74) *Attorney, Agent, or Firm* — Harness, Dickey and Pierce, P.L.C.

(57) ABSTRACT

The present invention relates to a new process for preparing brivaracetam. (Ib)

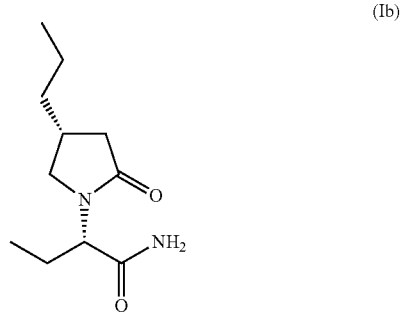

(Ib)

9 Claims, No Drawings

PROCESS FOR PREPARING BRIVARACETAM

CROSS-REFERENCE TO RELATED APPLICATIONS

This patent application is a U.S. National Phase of PCT/EP2016/075935, filed 27 Oct. 2016, which claims priority to EP 15192760.5, filed on 3 Nov. 2015. The entire disclosures of each of the above recited applications are incorporated herein by reference.

Brivaracetam is a diastereomer having been designated by either of the following names ((2S)-2-((4R)-2-oxo-4-n-propyl-1-pyrrolidinyl) butanamide or (2S)-2-[(4R)-2-oxo-4-propyltetrahydro-1H-pyrrol-1-yl]butanamide (Ib). The compound is a new anti-epileptic/anti-convulsive that was first disclosed in WO 01/62726.

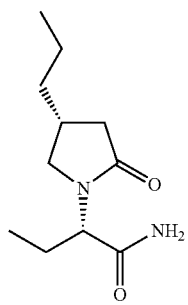
(Ib)

A method of synthesis is equally disclosed in WO 01/62726, said method involves the following two steps.

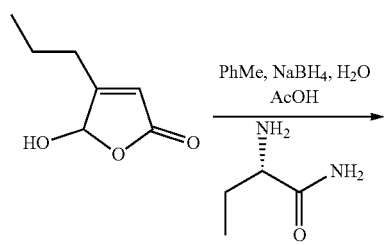

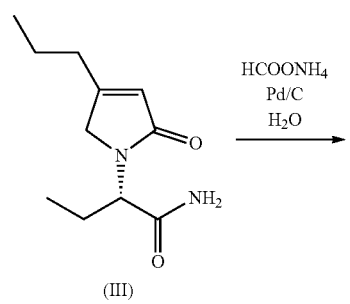
(III)

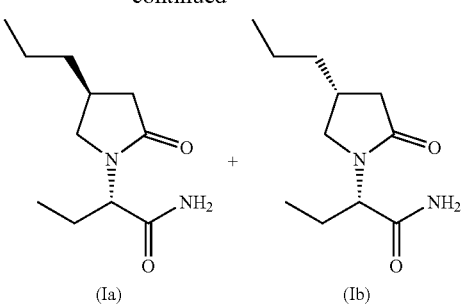
(Ia)     (Ib)

5-hydroxy-4-propyl-furan-2-one (373) could be obtained according to Bourguignon et al in the Journal of Organic Chemistry (1981), 46(24), 4889. The above method thus comprises

- a reductive amination step using 5-2-aminobutyramide yielding the unsaturated intermediate compound (III), as well as
- a hydrogenolysis step using NH$_4$COOH yielding the diastereomers (Ia) & (Ib).

An improved method for manufacturing brivaracetam is disclosed in WO 2005/028435, consisting of the following steps:

Step 1: Obtention of 5-hydroxy-4-n-propyl-furan-2-one Through Condensation of Valeraldehyde with Glyoxylic Acid

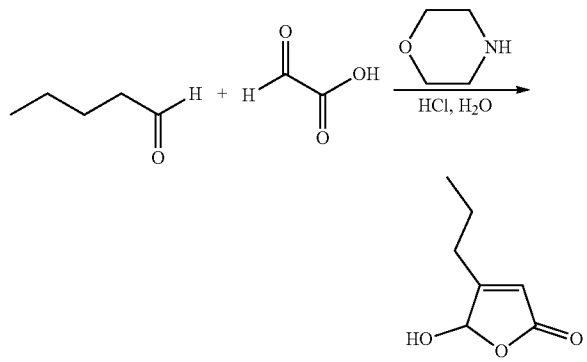

Step 2: Obtention of (2S)-2-((4R)-2-oxo-4-n-propyl-1-pyrrolidinyl)butanamide and (2S)-2-((4S)-2-oxo-4-n-propyl-1-pyrrolidinyl)butanamide

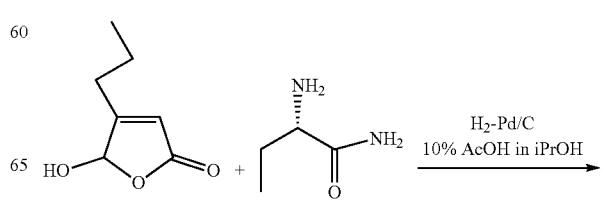

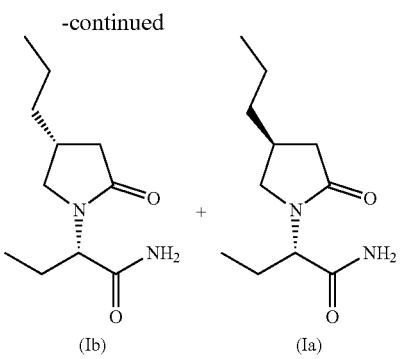

Said step 2 combines the reductive amination step as well as the hydrogenolysis step disclosed in WO 01/62726 in a one-pot reaction. The individual diastereomers obtained therefrom may then be separated, e.g. through chiral MCC.

Importantly, the methods disclosed in the art involve a non-asymmetric (heterogeneous) hydrogenation step. A 50/50 diastereomeric mixture of compound of formula (Ib) and (Ia) is obtained.

The objective of the present invention consists in the provision of an improved, i.e. more economical approach for preparing brivaracetam.

SUMMARY OF THE INVENTION

The present invention relates to a new method for the preparation of brivaracetam, said method comprises an asymmetric (heterogeneous) hydrogenation step. Brivaracetam is obtained in an enriched amount.

DETAILED DESCRIPTION OF THE INVENTION

The present invention pertains to the synthesis of (2S)-2-((4R)-2-oxo-4-n-propyl-1-pyrrolidinyl)butanamide in an enriched amount through catalytic reduction by performing the following reaction:

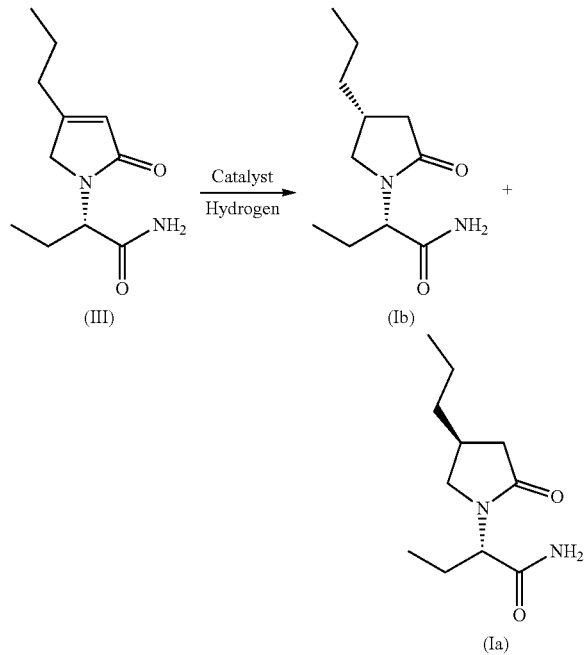

The catalytic reduction is performed in a polar solvent (including water, methanol, ethanol, 1-propanol, 1-butanol or a mixture of water and cited alcohols) or in a polar aprotic solvent (including acetonitrile, ethyl acetate) or in an apolar solvent (including toluene), typically in water using as catalytic systems (herein referred to as "Catalyst") either a Pt/C or a Pd/C or a Ir/CaCO$_3$ system (such catalytic systems are commercially available).

The hydrogen pressure is usually adjusted at any value between 5-40 bars. Most preferred is a hydrogen pressure below 10 bars.

Typical reaction temperatures are between 20-60° C. Preferred reaction temperatures are 20-25° C.

Typical amounts of Pt (mol %) are 0.5-1.5 mol %. A preferred amount of Pt is 0.5 mol %.

Typical amounts of Pd (mol %) are 0.5-1.5 mol %. A preferred amount of Pd is 0.5 mol %.

Typical amounts of Ir (mol %) are 0.5-1.5 mol %. A preferred amount is Ir is 0.5 mol %.

In specific embodiments, either of the following catalytic systems (Catalyst) may be used:

Pt/C; with the addition of formic acid or citric acid, typically in an amount of 0.25-10 eq, in one embodiment between 1-6 eq, in another embodiment between 1.5 to 3 eq, in a preferred embodiment in amount of 2 eq;

Pd/C; with the addition of citric acid or formic acid, typically in an amount of 0.25-10 eq, in one embodiment between 1-6 eq, in another embodiment between 1.5 to 3 eq, in a preferred embodiment in amount of 2 eq;

Ir/CaCO$_3$ with the addition of formic acid or citric acid, typically in an amount of 0.25-10 eq, in one embodiment between 1-6 eq, in another embodiment between 1.5 to 3 eq, in a preferred embodiment in amount of 2 eq.

By one equivalent (eq) it is meant one molar equivalent with respect to substrate compound (III).

In specific embodiments, either of the following catalytic systems (Catalyst) may be used:

Pt/C; with the addition of formic acid, typically in an amount of 0.25-10 eq, in one embodiment between 1-6 eq, in another embodiment between 1.5 to 3 eq, in a preferred embodiment in amount of 2 eq;

Pd/C; with the addition of citric acid, typically in an amount of 0.25-10 eq, in one embodiment between 1-6 eq, in another embodiment between 1.5 to 3 eq, in a preferred embodiment in amount of 2 eq;

Ir/CaCO$_3$ with the addition of formic acid, typically in an amount of 0.25-10 eq, in one embodiment between 1-6 eq, in another embodiment between 1.5 to 3 eq, in a preferred embodiment in amount of 2 eq.

Any preferred embodiment with regard to C (charcoal). C means activated charcoal. (the charge of metal on C tested was 3%, 5%, 10% and 20%

By enriched amount of brivaracetam it is meant that the above synthetic conditions allow a stereoselectivity in favor of the brivaracetam diastereomer ranging from 78.5/21.5 to 83/17 ratio or 57-66% diastereomeric excess (d.e.) which is a significant improvement over the methods used so far leading to a 50/50 ratio or 0% d.e.

Very surprisingly, such significantly improved stereoselectivity is achieved by using the conditions described above, in particular in view of the specific selection of formic acid or citric acid.

One way for obtaining the precursor (2S)-4,5-dehydro-(2-oxo-4-n-propyl-1-pyrrolidinyl)-2-butanamide (III) would be by following the following preparatory sequence:

Step 1: Synthesis of 5-hydroxy-4-n-propyl-furan-2-one (II)

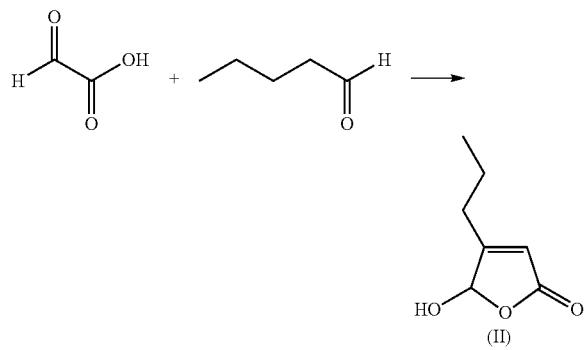

Step 2: Synthesis of (2S)-4,5-dehydro-(2-oxo-4-n-propyl-1-pyrrolidinyl)-2-butanamide (III)

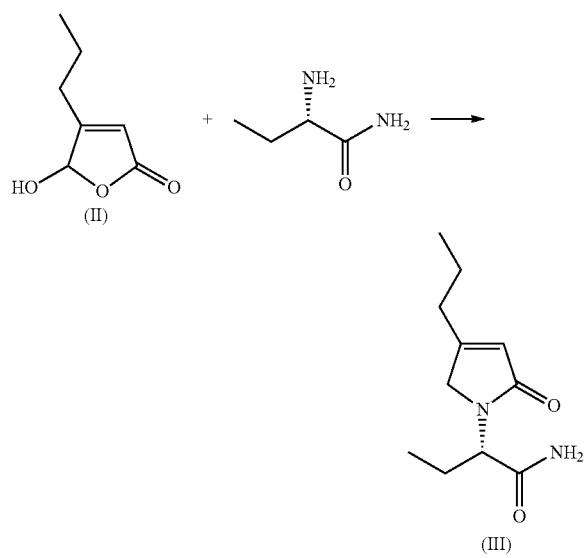

The final product obtained may still be subjected to further resolution or to a separation by MCC in order to obtain the brivaracetam diastereomer in a ratio of greater than 97/3, or 99/1.

In order to obtain essentially pure brivaracetam enantiomer (>98% d.e), a chromatographic separation may be performed. The chromatographic separation of the two diastereoisomers obtained in step 3 is performed using:

Chiralpak® IC as a chiral stationary phase, and a THF/n-heptan mixture (50/50 v/v) as mobile phase, or Chiralpak® AD as a chiral stationary phase, and a acetonitrile/methanol mixture (70/30 v/v) as mobile phase typically at a temperature of 25±2° C. The crude (2S)-2-((4R)-2-oxo-4-n-propyl-1-pyrrolidinyl)-butanamide thus obtained is purified in isopropylacetate, yielding pure (2S)-2-((4R)-2-oxo-4-n-propyl-1-pyrrolidinyl)butanamide.

EXAMPLES

Example 1: Synthesis of 5-hydroxy-4-propyl-furan-2-one, (II) (Step 1)

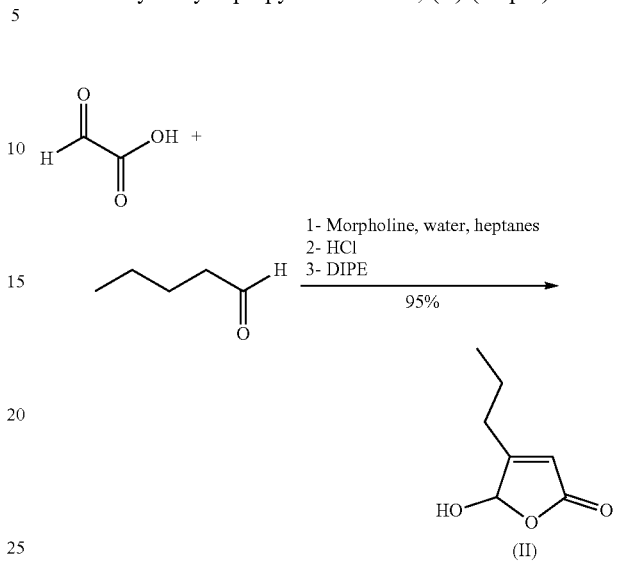

Example of industrial batch. All quantities of material were calculated with respect to the glyoxylic acid content of the 50% w/w glyoxylic acid solution used.

Heptane (1285 kg, 1889 L, 4.04 vol) and morpholine (595 L, 601.3 kg, 6902 mol, 1.09 eq) were charged in the reactor. After addition of morpholine, the equipment was rinsed with heptanes (20 L, 0.04 vol). The solution was stirred at 22-23° C. for 10 min, before being cooled to 4.4° C.

A 50% aqueous solution of glyoxylic acid (935 kg, 6318 mol, 1.0 eq) was slowly added while maintaining the temperature below 40° C. After addition of glyoxylic acid, the equipment was rinsed with heptanes (20 L, 0.04 vol). The medium was stirred for 2 hours at a temperature between 30.9 and 23.8° C. Valeraldehyde (706 L, 576.8 kg, 6697 mol, 1.06 eq) was then slowly added to the medium while maintaining the temperature below 40° C.

After addition of valeraldehyde, the equipment was rinsed with heptanes (40 L, 0.08 vol). The reactor contents were heated between 40.1 and 41.7° C. for 18 hours 04 minutes. The medium was then cooled to 22.8° C. and an aqueous solution of hydrochloric acid (1168 L, 1.73 eq) was added while keeping the temperature between 23.5 and 25.0° C.; the medium was stirred for 4 hours.

The medium was allowed to separate and the organic phase was removed. The aqueous phase was washed with heptanes (3×943 L, 3×2 vol). Diisopropyl ether (1322 kg, 1888 L, 4.04 vol) was added to the aqueous phase followed by solid sodium carbonate (199 kg) until a pH value of 0.4 was reached. The medium was allowed to separate and the organic phase was removed. Compound (II) was extracted from the aqueous phase with diisopropyl ether (2×530 kg, 2×756 L, 2×1.6 vol). The combined organic phases were washed with a 20% w/w aqueous solution of sodium chloride (944.2 kg, 1.6 vol). The organic layer was then dried by azeotropic distillation under vacuum at a jacket temperature of maximum 40° C. and filtered. The solution was finally concentrated under vacuum below 40° C. and a polish filtration through a 10 μm cartridge filter was performed. The total mass of solution (934.9 kg) was corrected for the water content (3.7%) and the DIPE content (3.8%) to give 864.8 kg of compound (II) (6084 mol, 96.3% yield).

Example 2: Provision of the Free Base of (S)-2-aminobutanamide hydrochloride, (S)-ABA.HCl

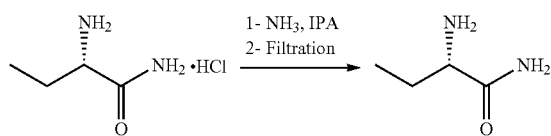

Example of industrial batch. All quantities of material were calculated with respect to (S)-2-aminobutanamide hydrochloride unless otherwise stated.

(S)-2-Aminobutanamide hydrochloride (500.0 kg, 3608 mol) was suspended in isopropanol (5000 L, 10 vol) at a temperature between 8.1 and 3.1° C. Cooling to 0±5° C. (S)-ABA free base was formed by an exothermic addition of ammonia (86 kg, 5050 mol, 1.4 eq). After 4 hours stirring at 0° C., the reaction conversion was checked for completion ((S)-ABA.HCl in the reaction medium, expressed as (S)-ABA base in the salt cake: 2.91% w/w).

Precipitated ammonium chloride salt was removed by filtration and the cake was washed with cold isopropanol (2×250 L, 2×0.5 vol). (S)-ABA free base was obtained in solution in isopropanol (4672.6 kg, 366.0 kg of (S)-ABA at 100%, 3584 mol, 99.3% yield). The (S)-ABA solution (4672.6 kg) was concentrated under vacuum below 40° C. to remove the excess ammonia until a residual concentration of 7 volumes was obtained with respect to compound (II). The (S)-ABA solution obtained is then telescoped with the Example 3.

Example 3: Synthesis of (2S)-(2-oxo-4-propyl-2,5-dihydro-pyrrol-1-yl)butanamide, (III)

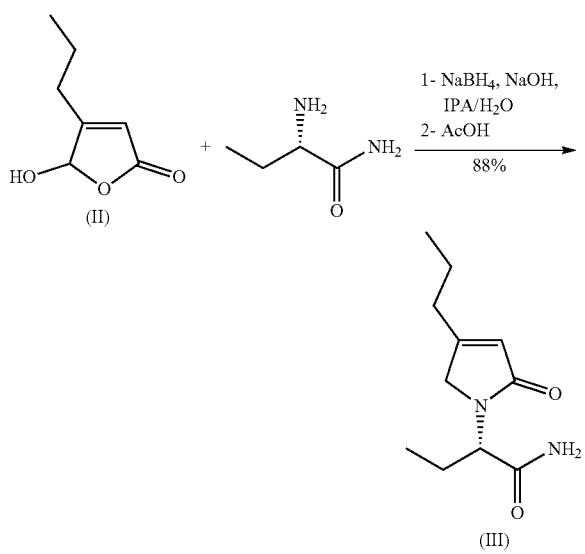

Compound (II) (732.6 g, 5.15 mol, 1.0 eq) is charged to a solution of (S)-ABA free base (599.31 g, 5.87 mol, 1.14 eq) in IPA (5248 mL, 7.2 vol). The reaction mixture is agitated at 40° C. for 1 hour then is cooled to 5° C. A prepared solution of sodium borohydride (116.7 g, 3.08 mol, 0.6 eq) in water (2175 mL, 3.0 vol) containing NaOH 50%-w/w in water (5.6 g, 0.07 mol, 0.014 eq) is added maintaining the internal temperature below 25° C. A 1 hour post stirring time is applied. Acetone (980 mL, 13.35 mol, 2.6 eq) is added to quench excess of NaBH4 while maintaining the internal temperature below 30° C. The salts formed are eliminated by filtration. Acetic acid (145 mL, 0.2 vol) is added to the filtrate up to a pH comprised between 7 and 8 then the reaction mixture is heated to 50° C. for 16 hours. The mixture is cooled to 20° C. and solvents are removed by evaporation. The product is dissolved in water (1820 mL, 2.5 vol) and extracted in IPAC (2×2900 mL, 2×4.0 vol). IPAC is eliminated by evaporation to dryness to give crude Compound (III) (1008 g, 93%).

The crude product is taken in IPAC (2000 mL, 2.0 vol wrt crude Compound (III)) and heated to 50° C. n-Heptane (1000 mL, 1 vol wrt crude Compound (III)) is added maintaining the temperature at 50° C. The solution is cooled to 40° C., seeded with Compound (III) (1 g, 0.1%) and matured at 40° C. for 15 min. n-Heptane (1000 mL, 1 vol wrt crude Compound (III)) is added slowly and the reaction mixture cooled. When too thick, the reaction mixture is diluted with n-heptane (2000 mL, 2.0 vol) and cooled to 20° C. in 4 hours before isolation by filtration. The wet cake is washed with n-heptane (2×1000 mL, 2×1 vol) and dried at 40° C. under vacuum for 3 hours to give compound (III) as an off white solid (956 g, 88.3% yield).

Example 4: Synthesis of (2S)-(2-oxo-4-propyltetrahydro-1H-pyrrol-1-yl)butanamide, Mixture of the Two Diastereoisomers (Ia) and (Ib)

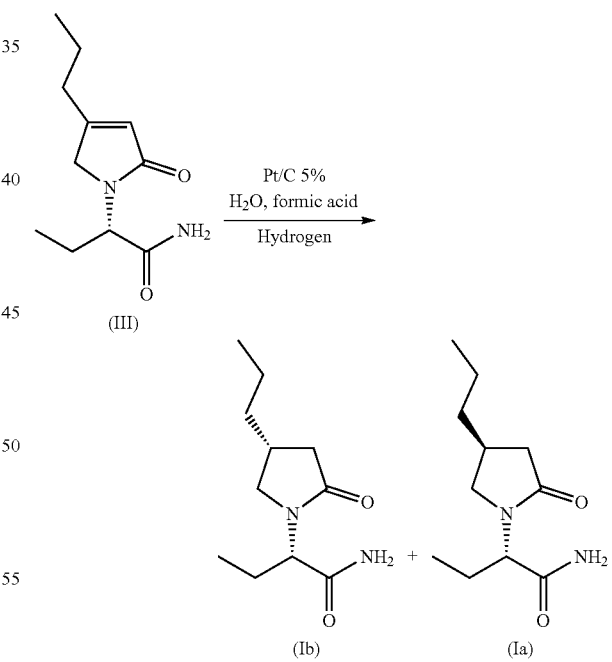

Option 1. All charges calculated with respect to compound (III) isolated in Example 3. The compound (III) (700 g, 3.33 mol, 1.0 eq) was dissolved in water (9.1 L, 13 vol) at 20° C. and then the formic acid (306 g, 6.66 mol, 2 eq) was added. After dissolution of the compound (III), the catalyst Pt/C 5% 54.3% wet (284 g, 33.3 mmol, 0.01 eq) was charged, under inert atmosphere. This suspension was stirred between 1 h and 2 h for pre-reduction until the end of the gas emission. This suspension was charged into the 20

L stainless steel reactor, equipped with a hollow shaft stirrer. The recipient containing the suspension was rinsed with water (1.4 L, 2 vol) and then transferred into the reactor to reach the final dilution of 15 vol.

Inerting Procedure:
Purge 1 time with inert gas pressure (9 barg/10 bara) without stirring
Purge 3 times with inert gas pressure (9 barg/10 bara) with stirring (1000 rpm)
Purge 3 times with hydrogen pressure (9 barg/10 bara) with stirring (1000 rpm)

The mixture was post-stirred at 20° C. till end of hydrogen consumption: typically 2 h under hydrogen pressure (9 barg/10 bara). The pressure was released to atmospheric pressure and the mixture was purged three times with inert gas pressure (9 barg/10 bara) with stirring (1000 rpm).

2 h reaction time: conversion 99.5%, d.e.=61%

The reaction mixture was filtered (typically 30 min) over pre-wet celite (~150 g), the cake was washed two times with water (2×700 ml, 2×1 vol). An additional wash of the catalyst with methanol (2×700 mL, 2×1 vol) allows to recover all the material from the catalyst. After evaporation, the methanol residue was engaged into the step of quench. The combined filtrate and washes (2<pH<3) were charged to a reactor for the neutralization. The sodium bicarbonate (573 g, 6.82 mol, 2.05 eq) was added by portion (typically 1 h 30) to control the gas emission (endothermic) at ~20° C. to reach a pH comprised between 7 and 8. The mixture was post-stirred till the end of the gas emission (typically 1 h).

The aqueous yellowish solution was then concentrated under vacuum at 40° C. to reach a dilution of 5 vol (8.4 L/12 vol of water was typically distilled over 9 h) to perform the extractions. The formation of a biphasic mixture during the concentration is observed. The product was extracted three times with IPAC (3×2.1 L, 3×3 vol). The combined organic phases were washed with water (350 mL, 0.5 vol).

The yellowish organic layer was evaporated under vacuum at 40° C. to dryness (typically 7 h) leading to an off-white solid. This solid was dried under vacuum (10 mbar) at 40° C. for 16 h to give the enriched mixture of the two stereoisomers (Ib) and (Ia), (610 g, 2.87 mol, 86.2% yield, 61% d.e., 99.2%-a).

Option 2 (example from optimal conditions demonstrated at laboratory scale). All charges calculated with respect to compound (III) isolated in step 2b.

The compound (III) (15 g, 71.3 mmol, 1.0 eq) was dissolved in water (65 mL, 4.3 vol) at 20° C. and then the formic acid (6.57 g, 142.7 mmol, 2 eq) was added. After dissolution of the compound (III), the catalyst Pt/C 5% 54.3% wet (3.05 g, 0.36 mmol, 0.005 eq) was charged, under inert atmosphere. This suspension was stirred between 1 h and 2 h for pre-reduction until the end of the gas emission. This suspension was charged into the 150 mL glass reactor, equipped with a hollow shaft stirrer. The recipient containing the suspension was rinsed with water (10 mL, 0.7 vol) and then transferred into the reactor to reach the final dilution of 5 vol.

Inerting Procedure:
Purge 1 time with inert gas pressure (9 barg/10 bara) without stirring
Purge 3 times with inert gas pressure (9 barg/10 bara) with stirring (1000 rpm)
Purge 3 times with hydrogen pressure (9 barg/10 bara) with stirring (1000 rpm)

The mixture was post-stirred at 20° C. till end of hydrogen consumption (typically NLT 6 h) under hydrogen pressure (9 barg/10 bara). The pressure was released to atmospheric pressure and the mixture was purged three times with inert gas pressure (9 barg/10 bara) with stirring (1000 rpm).

6 h reaction time: conversion 99.4%, d.e.=61%

The reaction mixture was filtered over pre-wet celite (~1 g), the cake was washed two times with water (2×7.5 mL, 2×0.5 vol) and one time with IPAC (15 mL, 1 vol) to recover all the product. The filtrate and the three washes (2<pH<3) were charged to a reactor for the neutralization. The sodium bicarbonate (12.3 g, 146.2 mmol, 2.05 eq.) was added by portion (typically 1 h30) to control the gas emission (endothermic) at ~20° C. to reach a pH comprised between 7 and 8. The mixture was post-stirred till the end of the gas emission (typically 1 h).

After the quench, IPAC (30 mL, 2 vol) was added and the phases separated. The product was extracted two additional times with IPAC (2×45 mL, 3×3 vol). The three organic phases were combined and washed by water (7.5 mL, 0.5 vol). The yellowish organic layer was evaporated to dryness under vacuum at 40° C. leading to the enriched mixture of the two diastereoisomers (Ia) and (Ib) as an off-white solid (12.5 g, 58.9 mmol, 83% yield, 61% d.e., 99.2%-a).

Example 5: Synthesis of Crude (2S)-2-[(4R)-2-Oxo-4-propyltetrahydro-1H-pyrrol-1-yl]butanamide, Crude (Ib)

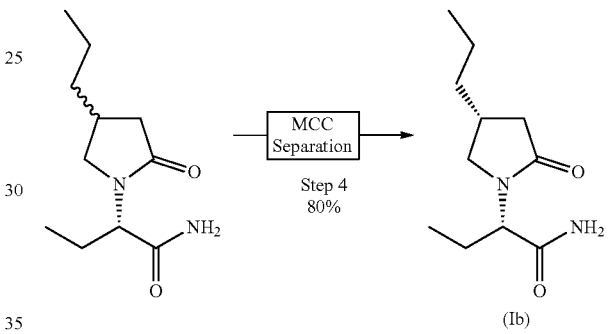

The mixture of the two diastereoisomers (Ia) and (Ib) obtained in Example 5, ratio 80/20 (500 g, 1 eq) is separated by multi-column continuous chromatography (MCC) using the following chiral stationary phase and eluent system:
Chiralpak® IC, THF/n-heptan (50/50 v/v), or
Chiralpak® AD, acetonitrile/methanol (70/30 v/v)

The raffinate stream or the extract stream are evaporated to dryness to give crude compound (Ib) (400 g, 80% yield).

Example 6: Synthesis of (2S)-2-[(4R)-2-Oxo-4-propyltetrahydro-1H-pyrrol-1-yl]butanamide, Compound (Ib)

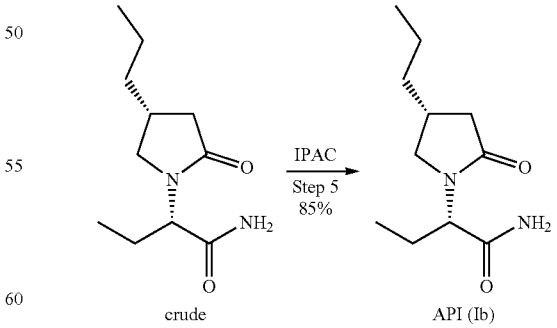

Example of industrial batch. All quantities of material were calculated with respect to crude compound (Ib).

Isopropyl acetate (224 L, 0.7 vol) was charged into the reactor and heated to 20° C. Crude compound (Ib) (319.4 kg, 1 eq) was then added followed by the addition of the rest of isopropyl acetate (96 L, 0.3 vol). The medium was stirred at a rate of 50 rpm and a temperature of 20° C. for 2 hours. The suspension was centrifuged at 20° C. in two loads and was dried under vacuum until an internal temperature of 38.5° C. was reached for a pressure of 10.3 mbar. The dryer contents were then cooled before being discharged. Dried brivaracetam API was finally milled on a 1 mm sieve. The final mass of brivaracetam was 272.7 kg (yield: 85.4%).

The invention claimed is:

1. A process for the preparation of (2S)-2-[(4R)-2-oxo-4-propyltetrahydro-1H-pyrrol-1-yl]butanamide (brivaracetam) in an enriched amount ranging from a 78.5/21.5 to 83/17 ratio in favor of the brivaracetam diastereomer, through catalytic reduction performed according to the following reaction:

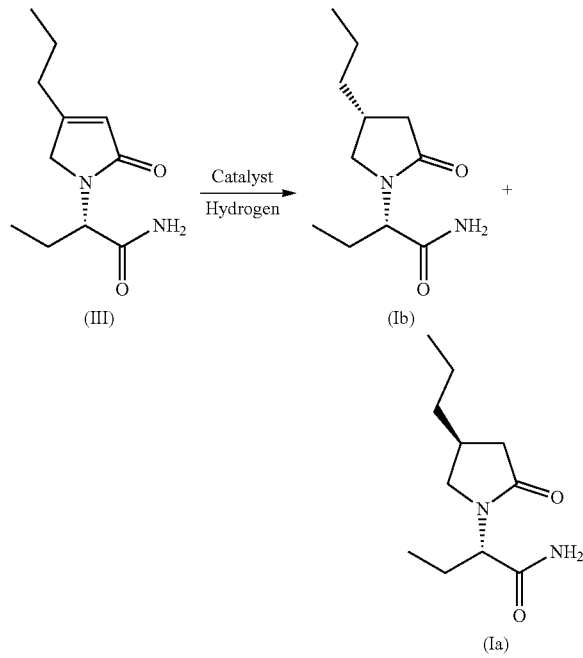

whereby the Catalyst is either of the following:

Pt/C; with the addition of formic acid or citric acid;

Pd/C; with the addition of citric acid or formic acid;

Ir/CaCO$_3$ with the addition of formic acid or citric acid.

2. The process according to claim 1, wherein the Catalyst is either of the following:

Pt/C; with the addition of formic acid;

Pd/C; with the addition of citric acid;

Ir/CaCO$_3$ with the addition of formic acid.

3. The process according to claim 1, which is performed in a polar solvent or in a polar aprotic solvent or in an apolar solvent.

4. The process according to claim 3, which is performed in water.

5. The process according to claim 1, wherein the hydrogen pressure is usually adjusted at any value between 5-40 bars.

6. The process according to claim 1, wherein Pt/C; with the addition of formic acid, in an amount of 2 eq is used as catalytic system (Catalyst).

7. The process according to claim 1, wherein Pd/C; with the addition of citric acid, in an amount of 2 eq is used as catalytic system (Catalyst).

8. The process according to claim 1, wherein Ir/CaCO$_3$ with the addition of formic acid, in an amount of 2 eq is used as catalytic system (Catalyst).

9. A process for the preparation of an essentially pure (2S)-2-[(4R)-2-oxo-4-propyltetrahydro-1H-pyrrol-1-yl]butanamide (brivaracetam) having a ratio of at least 97/3, through catalytic reduction performed according to claim 1 followed by a MCC.

* * * * *

UNITED STATES PATENT AND TRADEMARK OFFICE
CERTIFICATE OF CORRECTION

PATENT NO. : 10,421,717 B2
APPLICATION NO. : 15/772607
DATED : September 24, 2019
INVENTOR(S) : Thierry Defrance, Jean Septavaux and Didier Nuel It is certified that error appears in the above-identified patent and that said Letters Patent is hereby corrected as shown below:

On the Title Page

Item [72], Line 2, replace "Marseilles" with --Marseille--;

Item [72], Line 3, replace "Marseilles" with --Marseille--;

In the Specification

Column 2, Line 20, replace "5-2-aminobutyramide" with --S-2-aminobutyramide--.

Signed and Sealed this
Seventh Day of July, 2020

Andrei Iancu
*Director of the United States Patent and Trademark Office*